United States Patent
Nakada et al.

(10) Patent No.: US 6,846,963 B2
(45) Date of Patent: Jan. 25, 2005

(54) PROCESS FOR PRODUCING 1,1,1,3,3-PENTAFLUOROPROPANE

(75) Inventors: Tatsuo Nakada, Osaka (JP); Seiji Takubo, Osaka (JP); Toshikazu Yoshimura, Osaka (JP); Takashi Shibanuma, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 10/775,167

(22) Filed: Feb. 11, 2004

(65) Prior Publication Data

US 2004/0162451 A1 Aug. 19, 2004

Related U.S. Application Data

(62) Division of application No. 10/130,116, filed as application No. PCT/JP00/08002 on Nov. 14, 2000, now abandoned.

(30) Foreign Application Priority Data

Nov. 15, 1999 (JP) .......................................... 11-323971

(51) Int. Cl.$^7$ ....................... C07C 17/013; C07C 17/06; C07C 17/20; C07C 19/08; C07C 19/10

(52) U.S. Cl. ....................... 570/167; 570/164; 570/165; 570/166

(58) Field of Search ................................. 570/167, 164, 570/165, 166

(56) References Cited

FOREIGN PATENT DOCUMENTS

| EP | 0 729 932 A1 | 9/1996 |
|----|--------------|--------|
| EP | 0 921 109 A1 | 6/1999 |
| JP | 9-268141 | 10/1997 |
| JP | 10-17501 | 1/1998 |
| JP | 10-101594 | 4/1998 |
| WO | WO 96/01797 | 1/1996 |
| WO | WO 99/26720 | 6/1999 |

*Primary Examiner*—Elvis O. Price
(74) *Attorney, Agent, or Firm*—Birch, Stewart, Kolasch & Birch, LLP

(57) ABSTRACT

In a process for producing 1,1,1,3,3-pentafluoropropane which has a liquid-phase reaction step for fluorination of 1,1,1,3,3-pentahalopropane (wherein at least one of halogen atoms is not fluorine) with HF in the presence of antimony pentahalide catalyst in a reactor to obtain a reaction mixture comprising 1,1,1,3,3-pentafluoropropane and the antimony pentahalide catalyst, the fluorination is conducted at a reaction temperature less than 50° C.

4 Claims, 1 Drawing Sheet

PROCESS FOR PRODUCING 1,1,1,3,3-PENTAFLUOROPROPANE

CROSS-REFERENCE TO RELATED APPLICATIONS

This application is a Rule 1.53(b) divisional of application Ser. No. 10/130,116, filed on May 15, 2002, now abandoned which is the National Phase under 35 U.S.C. § 371 of PCT International Application No. PCT/JP00/08002, which has an International filing date of Nov. 14, 2000, and which designated the U.S. PCT/JP00/08002 claims priority on Japanese Application No. 11-323971 filed on Nov. 15, 1999. The contents of each of these applications is hereby incorporated by reference.

TECHNICAL FIELD

The present invention relates to a process for producing 1,1,1,3,3-pentafluoropropane (hereinafter also referred to as "R-245fa") by reacting 1,1,1,3,3-pentahalopropane (wherein at least one of the halogen atoms is not fluorine, and this is also applicable in the specification unless otherwise specified) with hydrogen fluoride (HF).

BACKGROUND ART

Since 1,1,1,3,3-pentafluoropropane is available as an HFC (hydrofluoro carbon) foaming agent, a coolant or a propellant without any concern for destroying an ozone shield, and has industrial importance in view of an alternative to what is called flon gas, there is an urgent need to establish a process for producing such compound.

As a process for producing 1,1,1,3,3-pentafluoropropane, there is a known process utilizing a fluorination reaction of 1,1,1,3,3-pentachloropropane, which belongs to 1,1,1,3,3-pentahalopropane, with hydrogen fluoride. Such a fluorination reaction is generally conducted at a relatively high temperature and proceeded in a liquid phase while being supplied with an excess amount of HF with respect to 1,1,1,3,3-pentachloropropane as a raw material (or starting material). After the reaction is sufficiently proceeded, a reaction effluent (or reaction mixture) comprising unreacted HF, R-245fa as an aimed product and intermediate fluorides (such as 1,1,1,3-tetrafluoro-3-chloropropane, 1,1,1-trifluoro-3,3-dichloropropane and so on), which reaction effluent may exist in a liquid or gas state, is heated to be gasified in whole. Thus resultant material is drawn from a reactor in a gas phase, and R-245fa is obtained by subjecting the gaseous material drawn from the reactor to separation and refinement.

The fluorination reaction as described above is usually conducted in the presence of catalyst considering the yield of R-245fa. WO96/01797 discloses that Lewis acid catalyst such as antimony pentahalide can be used as the catalyst for the reaction.

It is necessary to set a reaction temperature appropriately since it is generally an important factor for determining a reaction rate as well as a scale of the reactor. As mentioned above, the fluorination reaction of 1,1,1,3,3-pentachloropropane is conducted at a relatively high temperature in order to increase the reaction rate and to gasify the reaction effluent. The gasification of the reaction effluent is required to refine the reaction effluent directly by means of a distillation apparatus which is mounted on the reactor. A temperature not less than 50° C. and generally not less than 100° C. is selected as the reaction temperature in a conventional process for producing R-245fa, though the reaction temperature may depend on a reaction pressure.

The reaction effluent from the fluorination reaction described above containing at least R-245fa and unreacted HF is drawn out from the reactor in a gas phase and subjected to the separating and refining procedure through distillation. However, it is difficult to directly separate R-245fa from the reaction effluent by a simple operation of the distillation or the like because R-245fa forms an azeotropic mixture (or azeotrope) together with HF. In order to solve this problem, Japanese Patent Kokai publication H10-17501 owned by the applicant of the present application, for example, discloses a process for separating R-245fa from a mixture of R-245fa and HF with higher efficiency by utilizing extraction.

DISCLOSURE OF THE INVENTION

In a conventional process for producing R-245fa, a reactor which is made from a metal material having a high heat conductivity is used, and a reaction mixture in the form of a liquid phase (i.e. the reaction effluent in the liquid phase) existing in the reactor is heated through the wall of the reactor in order to increase the reaction rate and to supply an amount of heat to the reaction mixture (the reaction effluent) containing the aimed product from outside the reactor, which heat is needed to gasify it. However, the metal material(s) of the reactor is severely corroded when 1,1,1,3,3-pentachloropropane and HF are reacted at a high temperature in the presence of antimony pentahalide as the catalyst since the reaction solution has extremely high corrosiveness. There is no metal material which is not corroded by and is stable to the reaction solution in the long term at the relatively high temperature which is used in the conventional process. Thus, problems of a short lifetime of the reactor and of a high manufacturing cost are derived.

In order to solve the problems as described above, it is described in, for example, WO99/26720 to use a reaction apparatus having a double walled structure consisting of an outer container and an inner reactor which is located within the outer container wherein at least an inner surface of the reactor is lined with a resin.

The use of the reactor having a resin lining as described above can cope with the problems derived from the corrosion, but it is not a satisfactory way. The reason is as follows: It is very difficult to supply a sufficient amount of heat to the reaction mixture from outside for gasifying the mixture since resins generally have heat conductivity lower than that of metal materials. Particularly in a case of the reactor having a great capacity, a ratio of heat transfer ability (i.e. a contacting area of the reaction mixture with the wall of the reactor) to an amount of reaction mixture is lowered.

The present invention aims to provide a new process for producing 1,1,1,3,3-pentafluoropropane including a reaction step for fluorinating 1,1,1,3,3-pentahalopropane with HF in the presence of antimony pentahalide as catalyst, wherein the problems as described above can be alleviated and its manufacturing cost can be reduced.

A process for producing 1,1,1,3,3-pentafluoropropane of the present invention is characterized in that fluorination is proceeded at a reaction temperature less than 50° C. in a reaction step in a liquid phase wherein 1,1,1,3,3-pentahalopropane (wherein at least one of halogen atoms is not F, in other words, at least one of five halogen atoms is halogen atom other than F) is fluorinated with HF in the presence of antimony pentahalide as catalyst in a reactor to obtain a reaction mixture (or a reaction effluent) including at least 1,1,1,3,3-pentafluoropropane and antimony pentahalide as catalyst. According to the present invention, corrosion of a metal material(s) used for the reactor can be depressed because of the reaction temperature less than 50° C. It is noted that the phrase "reaction mixture (or reaction effluent)" in the present invention denotes a mixture in a liquid state obtained through the reaction step in the liquid phase described above, and contains at least 1,1,1,3,3-pentafluoropropane (R-245fa) as the aimed product and antimony pentahalide as catalyst, and generally further contains unreacted raw materials (i.e. 1,1,1,3,3-pentahalopropane and HF), intermediate fluorides and so on. The phrase "reaction temperature" denotes a temperature of a reaction system at which the liquid phase-reaction step described above is proceeded, and more concretely a temperature inside the reactor (especially a temperature of the liquid phase in the reactor).

We have found that a reaction for fluorinating 1,1,1,3,3-pentahalopropane with hydrogen fluoride in the presence of antimony pentahalide in a reactor (hereinafter, which reaction is simply referred to as a "fluorination reaction") proceeds with a high yield even at a low temperature less than 50° C. by selecting reaction conditions appropriately. Concretely, it is turned out that this can be attained by increasing the concentration of HF in the reaction system. In a preferred embodiment of the present invention, HF exists in the reaction system at an amount of not less than 5 times by mole based on that of antimony pentahalide through the fluorination reaction step.

In an embodiment of the present invention, after the reaction step described above, the reaction mixture (or the reaction effluent) is subjected to an extraction separation step wherein the reaction mixture and an extractant (or solvent) both in liquid state may be contacted and mixed with each other to separate 1,1,1,3,3-pentafluoropropane from the reaction mixture by liquid-liquid extraction separation. In the extraction separation step, the mixture obtained by contacting and mixing the reaction mixture and the extractant each other separates into an extractant phase and an HF phase which are immiscible liquid phases with each other. The HF phase results from a process wherein most of unreacted HF included in the reaction mixture forms a separate phase which is immiscible with the extractant phase without being extracted by the extractant. In addition to HF, substantially all of the antimony pentahalide catalyst is also distributed into the HF phase. More amount of 1,1,1,3,3-pentafluoropropane is distributed into the extractant phase than that into the HF phase, and less amount of HF is distributed into the extractant phase than that into the HF phase. Additionally, intermediate fluorides and 1,1,1,3,3-pentahalopropane except for R-245fa, both of which are contained in the reaction mixture, behave together with R-245fa and are distributed into the extractant phase at a larger amount than that into the HF phase. Therefore, it is possible by utilizing the extraction separation to separately distribute most of unreacted HF and antimony pentahalide as catalyst into the HF phase, and thereby to obtain the extractant phase which contains most of R-245fa produced through the reaction as well as a little amount of HF.

In an embodiment of the present invention, after the extraction separation step described above, the extractant phase is subjected to a distillation separation step wherein HF is distilled out in the form of an azeotropic mixture of 1,1,1,3,3-pentafluoropropane and HF existing in the extractant phase, and then 1,1,1,3,3-pentafluoropropane including substantially no HF is distilled out to obtain a fraction of 1,1,1,3,3-pentafluoropropane as well as another fraction comprising substantially no 1,1,1,3,3-pentafluoropropane as the remainder. Therefore, it is possible by utilizing the distillation separation to obtain high purity 1,1,1,3,3-pentafluoropropane including substantially no HF.

In an embodiment of the present invention, the extractant can be removed from the fraction comprising substantially no 1,1,1,3,3-pentafluoropropane which is obtained as the remainder in the distillation separation step described above, and the rest after the removal can be recycled to the reactor. On the other hand, thus removed extractant can be recycled for the extraction separation step. Alternatively, in the case of using 1,1,1,3,3-pentachloropropane as the extractant, the fraction comprising substantially no 1,1,1,3,3-pentafluoropropane, which fraction is obtained through the distillation separation step described above, contains only the starting material for the fluorination reaction and the intermediate fluorides. In this case, such fraction, therefore, can be recycled to the reactor in whole. Alternatively, a part of such fraction can be returned to the reactor and the remainder can be recycled for the extraction separation step.

The present invention includes for example various embodiments (Embodiments 1 to 12) as follows.

(Embodiment 1) A process for producing 1,1,1,3,3-pentafluoropropane which process comprises a liquid-phase reaction step for fluorination of 1,1,1,3,3-pentahalopropane (wherein at least one of halogen atoms is not F) with HF in the presence of antimony pentahalide as catalyst in a reactor to obtain a reaction mixture comprising at least 1,1,1,3,3-pentafluoropropane and antimony pentahalide as catalyst, wherein the fluorination is conducted at a reaction temperature less than 50° C.

(Embodiment 2) The process according to Embodiment 1, wherein the fluorination is conducted at a reaction temperature from −10 to 50° C.

(Embodiment 3) The process according to Embodiment 1 or 2, wherein HF exists in a reaction system in an amount of at least 5 times by mole as large as an amount of the antimony pentahalide during the reaction step.

(Embodiment 4) The process according to any one of Embodiments 1 to 3, wherein the reaction step is followed by subjecting the reaction mixture to an extraction separation step in which the reaction mixture and an extractant are contacted and mixed with each other while extracting 1,1,1,3,3-pentafluoropropane from the reaction mixture and then separated into an extractant phase and an HF phase, wherein an amount of 1,1,1,3,3-pentafluoropropane contained in the extractant phase is larger than that contained in the HF phase.

(Embodiment 5) The process according to any one of Embodiments 1 to 4, wherein each of the halogen atoms of 1,1,1,3,3-pentahalopropane is selected from a group consisting of F, Cl and Br.

(Embodiment 6) The process according to any one of Embodiments 1 to 4, wherein 1,1,1,3,3-pentahalopropane is 1,1,1,3,3-pentachloropropane, and the reaction mixture further comprises 1,1,1,3-tetrafluoro-3-chloropropane and 1,1,1-trifluoro-3,3-dichloro propane.

(Embodiment 7) The process according to Embodiment 4, wherein the extraction separation step is followed by subjecting the extractant phase to a distillation separation step in which HF is distilled out in the form of an azeotropic mixture of HF and 1,1,1,3,3-pentafluoropropane, and then 1,1,1,3,3-pentafluoropropane including substantially no HF is distilled out to obtain a fraction of 1,1,1,3,3-pentafluoropropane and another fraction comprising substantially no 1,1,1,3,3-pentafluoropropane as the remainder.

(Embodiment 8) The process according to Embodiment 7, wherein the distillation separation step is followed by removing the extractant from the fraction comprising substantially no 1,1,1,3,3-pentafluoropropane and recycling the rest of the fraction to the reactor.

(Embodiment 9) The process according to any one of Embodiments 4, 7, 8 as well as Embodiments 5 and 6 in case of both depending on Embodiment 4, wherein the extractant is 1,1,1,3,3-pentachloropropane.

(Embodiment 10) The process according to Embodiment 7, wherein the extractant is 1,1,1,3,3-pentachloropropane, and the distillation separation step is followed by recycling the another fraction comprising substantially no 1,1,1,3,3-pentafluoropropane to the reactor as it is.

(Embodiment 11) The process according to any one of Embodiments 4, 7 and 8 as well as Embodiments 5 and 6 in case of both depending on Embodiment 4, wherein the extractant is a solvent which is inert to the reaction of the fluorination.

(Embodiment 12) The process according to Embodiment 11, wherein the extractant is selected from a group consisting of fluorinated hydrocarbon compounds, fluorinated ether compounds and fluorinated alkylamine compounds.

BEST MODE FOR CARRYING OUT THE INVENTION

Figure 1:
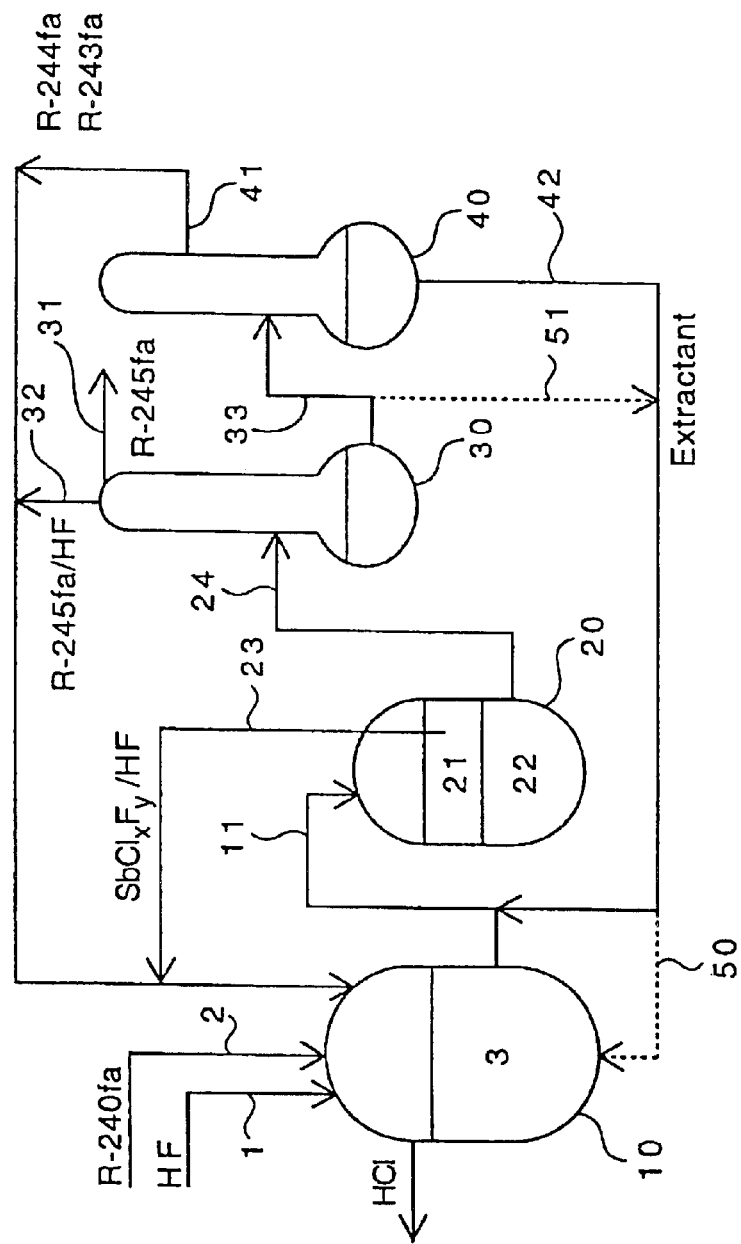
FIG. 1 shows a process diagram of one embodiment of the present invention.

Hereinafter, a process of the present invention will be described in detail. It is noted that the phrase "intermediate fluorides" through the specification denotes derivatives resulted by substituting at least one of halogen atoms of 1,1,1,3,3-pentahalopropane other than a fluorine atom with a fluorine atom (which derivatives excludes 1,1,1,3,3-pentafluoropropane). Additionally, the phrase "fluorinated products" through the specification denotes such intermediate fluorides and 1,1,1,3,3-pentafluoropropane as the aimed product.

1. Fluorination Reaction 1,1,1,3,3-pentahalopropane (wherein at least one of halogen atoms is other than F) is fluorinated with HF in the presence of antimony pentahalide(s) in a reactor to obtain a reaction mixture. The reaction mixture contains fluorinated products (1,1,1,3,3-pentafluoropropane and its intermediate fluorides), unreacted raw materials (1,1,1,3,3-pentahalopropane and HF) and antimony pentahalide. The fluorination reaction is conducted at a reaction temperature less than 50° C. As described above, an advantage of depressed corrosion of metal materials used for the reactor can be attained as long as the reaction temperature is less than 50° C. Furthermore, it is possible to select an optimum reaction temperature in a range less than 50° C. by considering a balance of reaction and corrosion rates. In view of reducing the corrosion rate, the reaction temperature is made as lower as possible, for example, at a temperature of 30° C. or less, preferably 25° C. or less, and more preferably 20° C. or less. In view of obtaining the reaction rate to a certain degree, the reaction temperature is preferably −10° C. or more. Thus, the reaction temperature is preferably −10° C. to 50° C., more preferably −10° C. to 30° C., most preferably −10° C. to 25° C., and especially −10° C. to 20° C.

In the case where the reaction step is followed by a liquid-liquid extraction separation step, it is preferable to set the reaction temperature while considering such extraction separation step. It is generally required to conduct the extraction at a relatively low temperature in order to achieve a high efficiency of the extraction separation and decrease a mutual solubility. For the purpose of dispensing with the temperature control of the reaction mixture by cooling or heating or for the purpose of minimizing thermal load on it under heating or cooling, it is preferable to previously set the reaction temperature equal or close to a temperature suited for the extraction. In other words, the temperature is preferably set at a temperature as low as possible so as to be suited for the extraction. On the contrary, it is not desirable to set the reaction temperature too low because such a temperature brings low reaction rate. As a result of consideration of these matters, it is preferable to set the reaction temperature in a range from −10° C. to 30° C.

The fluorination reaction proceeds in a liquid phase to form the reaction mixture, though 1,1,1,3,3-pentahalopropane and HF as the raw materials are supplied to the reactor either in a liquid phase or in a gas phase. The reaction mixture is generally in the form of a solution (Hereinafter, the reaction mixture in a liquid state is simply called as the "reaction solution"). 1,1,1,3,3-pentahalopropane and HF can be supplied continuously or in a batch mode process. The fluorination reaction may involve production of HCl, and thus produced HCl can be readily removed from the reaction solution since HCl is released into a gas phase. A pressure inside the reactor is for example, but not limited to, 0.1 to 1.0 MPa (abs.).

The halogen atoms of 1,1,1,3,3-pentahalopropane can be independently selected from a group consisting of F, Cl and Br. More specifically, 1,1,1,3,3-pentahalopropane is exemplified by 1,1,1,3,3-pentachloropropane and its derivatives which is resulted by substituting one to four chlorine atoms of 1,1,1,3,3-pentachloropropane with fluorine atoms, and 1,1,1-trifluoro-3,3-dibromopropane, 1,1,3,3-tetrafluoro-1-bromopropane and so on.

Antimony pentahalide which is used as the catalyst is expressed as the formula of $SbCl_xF_y$ (wherein $0 \leq x$, $y \leq 5$; $x+y=5$). The catalyst can be prepared by reacting $SbCl_5$ with HF. Furthermore, $SbCl_5$ itself or $SbF_5$ is also used as the catalyst. It is generally considered that these compounds have a constitution expressed as the formula of $HSbCl_xF_{y+1}$ in an atmosphere of HF. As to the formula $HSbCl_xF_{y+1}$, "x" and "y" are supposed to have a relationship of x<y, but they are variable depending on a reaction conditions. For example, "x" is preferably in a range of $3 \leq x \leq 5$.

It should be noted that "x" and "y" are not limited to integers, but they can be any real numbers as long as they satisfy the condition of $0 \leq x$, $y \leq 5$; and x+y=5. Therefore, the catalyst expressed as the formula of $SbCl_xF_y$ can be consists of one compound or mixture of plural compounds expressed as the formula of $SbCl_xF_y$. As an example, a mixture prepared by mixing $SbCl_5$ and $SbF_5$ at an arbitrary ratio (molar basis) to satisfy the formula of $SbCl_xF_y$ can be used as the catalyst.

As to the catalyst expressed as the formula of $SbCl_xF_y$, values of "x" and "y" after the reaction can be changed from those before the reaction as long as the values consistent with the conditions of $0 \leq x$, $y \leq 5$; and x+y=5.

HF preferably exists in the reaction system at an amount of not less than 5 times by mole as large as that of antimony pentahalide through the fluorination reaction step described above, and more preferably not less than 10 times by mole. In this context, the reaction system denotes a system (or a circumstance) in which the reaction proceeds, and it can be substantially regarded as the liquid phase in the reactor since an amount of the substance existing in the gas phase in the reactor is significantly smaller than that in the liquid phase. In addition, an amount of HF in the system is preferably not greater than 100 times by mole, more preferably not greater than 50 times by mole as large as that of antimony pentahalide.

The reaction proceeds with a high selectivity and a high yield when the amount of HF existing in the reaction system is not less than 5 times by mole based on that of antimony pentahalide which is supplied as the catalyst. A reaction system wherein the amount of HF is less than such amount and the concentration of the catalyst is rather high is not preferable since the selectivity of the fluorination reaction undesirably decreases. In addition to the above, when the reaction step is followed by an extraction separation step, the extraction is more difficult because the compatibility between the extractant and the reaction mixture increases. Thus, the amount of HF is preferably not less than 5 times by mole, and more preferably not less than 10 times by mole as large as that of antimony pentahalide.

On the other hand, when the amount of HF is too large, in other words, when the concentration of the catalyst is too low, it brings a low reaction rate resulting in a low yield. Thus, it is required to conduct the reaction in a state including HF at an amount of no greater than 100 times by mole, and preferably no greater than 50 times by mole as described above.

The amount of HF to be supplied can be varied as long as it is larger than a stoichiometrically necessary amount (i.e. an amount which is necessary to change the whole of 1,1,1,3,3-pentahalopropane into R-245fa) for producing R-245fa as the aimed product based on the amount of 1,1,1,3,3-pentahalopropane. Additionally, it is advantageous to set the amount of HF not greater than 2 times by mole as large as the necessary amount thereof described above.

The reactor can be made of a Ni-based material which has corrosion resistance. Concretely, the materials such as Hastelloy, Monel, Inconel and the like are exemplified. In a case where there is no need to supply heat from outside the reactor, a resin material having a low thermal conductivity can be used for the reactor or its lining. Such resin material may be, for example, a tetrafluoroethylene resin, a chlorotrifluoroethylene resin, a vinylidene fluoride resin, a PFA resin, or the like.

2. Extraction Separation

After the reaction step described above, the reaction mixture is transferred to an extraction separation step. In the extraction separation step, the reaction mixture is contacted and mixed with an extractant to extract 1,1,1,3,3-pentafluoropropane from the reaction mixture, and thereafter thus resultant mixture is separated into an extractant phase and an HF phase which are immiscible with each other. The extractant phase contains more amount of 1,1,1,3,3-pentafluoropropane than that in the HF phase, and the extractant phase preferably contains the most of 1,1,1,3,3-pentafluoropropane. The extractant phase further contains most of intermediate fluorides and unreacted 1,1,1,3,3-pentahalopropane and a little amount of HF. Such extraction separation is specifically referred to as liquid-liquid extraction separation, and it makes possible that the resultant mixture consisting of the reaction mixture and the extractant can be separated into the HF phase and the extractant phase, while distributing most of unreacted HF into the HF phase. According to the extraction separation step, it is possible to obtain a fraction containing 1,1,1,3,3-pentafluoropropane without subjecting the reaction mixture to a relatively high temperature (or without gasifying it).

The extraction separation step is important for reducing the heat which should be supplied to the reactor. According to such extraction separation, there is no need to make the reaction temperature high since R-245fa and HF can be separated without gasifying the reaction mixture as described above. On the contrary, a low temperature is suited by considering the following extraction. When the reaction temperature is set at a low temperature and there is no need to supply heat from outside the reactor, there also no need to consider the heat conductivity of the material of the reactor. Thus, the resinous material and the like can be used for a material of the reactor or the lining for the reactor as described above.

The fluorinated products (i.e. R-245fa as the aimed product and the intermediate fluorides), unreacted 1,1,1,3,3-pentahalopropane and the little amount of HF are extracted into the extractant phase. When a compound of 1,1,1,3,3-pentahalopropane containing no fluorine atom (hereinafter, which compound is referred to as "R-240fa") is used as the starting material, the intermediate fluorides produced through the fluorination reaction mainly contain "R-244fa" (wherein four halogen atoms of 1,1,1,3,3-pentahalopropane are substituted with fluorine atoms) and "R-243fa" (wherein three halogen atoms of 1,1,1,3,3-pentahalopropane are substituted with fluorine atoms). In the case where 1,1,1,3,3-pentachloropropane is used as the starting material, for example, the intermediate fluorides mainly contain 1,1,1,3-tetrafluoro-3-chloropropane and 1,1,1-trifluoro-3,3-dichloropropane and further contain other compounds having more chlorine atoms at a little amount. The ratios of these fluorinated products depend on reaction conditions such as the reaction temperature, a volume of the reaction solution and feeding rates of the raw materials.

An operation for the extraction is described in detail in the Japanese Patent Kokai No. 10-17501 described above, and extractants disclosed in it are preferably applicable to the present invention. The examples of the extractant include chlorinated hydrocarbon compounds, solvents which are inert to the fluorination reaction (such a solvent can be selected from a group consisting of fluorinated hydrocarbon compounds, fluorinated ether compounds and fluorinated amine compounds) as well as a mixture thereof can be used.

More specifically, suitable chlorinated hydrocarbon compounds include 1,1,1,3,3-pentachloropropane, hexachloropropene, trichloroethylene, perchloroethylene and the like. Specific examples of suitable fluorinated hydrocarbon compounds include perfluoro-2-methylpentane (sec-$C_6F_{14}$), perfluoro-n-hexane (n-$C_6F_{14}$), 43–10 mee (1,1,1,2,2,3,4,5,5,5-decafluoropentane), 1H-perfluoro-2-pentene, perfluoro-2-methyl-2-pentene, perfluoro-4-methyl-2-pentene, 1H-perfluorooctane (omega-H-perfluorooctane ($C_8F_{17}H$)), omega-H-perfluorohexane ($C_6F_{13}H$), perfluorocyclohexane, perfluoroheptane, perfluoropropane, perfluorobutane, pentadecafluoroheptane, perfluorodecalin and so on. Specific examples of suitable fluorinated ether compounds include methyl-1,1,2,3,3,3-hexafluoropropylether, ethyl-1,1,2,3,3,3-hexafluoropropylether, propyl-1,1,2,3,3,3-hexafluoropropylether, 1-methoxy-nonafluorobutane, 1-ethoxynonafluorobutane and so on. Specific examples of suitable fluorinated amine compounds include perfluorotributylamine, perfluoropentylamine, perfluoro-N-methylmorpholine and so on.

As to the extraction conditions, conditions disclosed in the Japanese Patent Kokai No. 10-17501 are applicable to the present invention. On both contacting and separating, for example, a temperature is kept in a range of −30 to 50° C., preferably −30 to 30° C., and more preferably −30 to 0° C., and a pressure (absolute pressure) is kept at or over the atmospheric pressure (1 atm, i.e. 0.101 MPa), preferably in a range of 1 to 30 atm, i.e. 0.101 to 3.04 MPa. A solvent ratio "S/F" (weight basis), which is a ratio of the weight of the extractant "S" to the weight of the reaction mixture "F", is generally in a range of 0.5 to 2.

A manner of the extraction is not limited, and any appropriate manner can be applied. For example, the extraction may be conducted in a manner such as a batch mode process, a countercurrent contacting operation and so on.

The HF phase containing antimony pentahalide, which phase is obtained by the extraction separation step, can be recycled for the fluorination reaction step after removing impurities, if necessary.

3. Distillation Separation

After the extraction separation step described above, the extractant phase is transferred to a distillation separation step. The extractant phase, which is separated through the extraction separation, includes a little amount of HF in addition to 1,1,1,3,3-pentafluoropropane and the like. In the distillation separation step, HF is distilled in the form of an azeotrope (or azeotropic mixture) of HF and 1,1,1,3,3-pentafluoropropane, and then a fraction of 1,1,1,3,3-pentafluoropropane including substantially no HF is distilled. As a result, there is obtained the fraction of 1,1,1,3,3-pentafluoropropane as the aimed product as well as a residual fraction including substantially no 1,1,1,3,3-pentafluoropropane. According to such an azeotropic distillation, HF distributed into the extractant phase at a relatively small amount can be readily removed as the azeotrope together with 1,1,1,3,3-pentafluoropropane.

Conventionally, it was difficult to directly separate R-245fa from the reaction mixture containing a much amount of HF by the distillation process since 1,1,1,3,3-pentafluoropropane and HF form an azeotrope as described in the Japanese Patent Kokai No. 10-17501. In the present invention contrary to the above, since most of HF had previously been removed from the reaction mixture by the extraction process as described above, remaining HF which is contained at a relatively small amount in the extractant phase may be removed as the azeotrope through the distillation. Thereafter 1,1,1,3,3-pentafluoropropane including substantially no HF can be readily obtained with a high purity. The phrase "including substantially no HF" denotes that the content of HF is not greater than 0.2% by weight, and preferably 0 to 0.1% by weight.

The separation of the fraction of 1,1,1,3,3-pentafluoropropane including substantially no HF from the extraction phase as described above can be conducted in a batch mode process or a continuous mode process. Furthermore, the distillation separation can be conducted by means of one distillation column or two distillation columns in parts.

In case of using one distillation column, as an example, R-245fa (1,1,1,3,3-pentafluoropropane) can be separated in a batch mode process by distilling the azeotrope of HF and R-245fa from the top of the column at first, followed by distilling the fraction of R-245fa including substantially no HF from the top. In case of using two distillation columns, R-245fa can be separated in a continuous mode process by distilling the azeotrope of HF and R-245fa from the top of the first column, transferring the bottom product of the first column to the second column, and distilling the fraction of R-245fa including substantially no HF from the top of the second column. Additionally, even in the case of using a single distillation column, R-245fa can be separated in a continuous mode process by distilling the azeotrope from the top of the column, and distilling the fraction of R-245fa including substantially no HF from the middle of the column.

The extractant phase contains the intermediate fluorides and the unreacted 1,1,1,3,3-pentahalopropane in addition to the little amount of HF and the aimed product of R-245fa. After the removal of HF in the form of the azeotrope, the intermediate fluorides and 1,1,1,3,3-pentahalopropane can be removed from the aimed product of R-245fa by a distillation operation similar to that for removal of HF.

As an example, the azeotrope of HF and 1,1,1,3,3-pentahalopropane is distilled out from the top of the distillation column, and then 1,1,1,3,3-pentafluoropropane including substantially no HF is distilled out from the top. On the other hand, a mixture of the intermediate fluorides, unreacted 1,1,1,3,3-pentahalopropane and the extractant can be drained out as the bottom product of the column. It is noted that any appropriate distillation manner and conditions are applicable, and the present invention is not limited to a certain one.

The azeotrope (containing HF) obtained from the distillation separation step can be recycled for the fluorination reaction step and/or the extraction separation step.

4. Recycle

After the distillation separation step described above, the fraction including substantially no 1,1,1,3,3-pentafluoropropane (the bottom product) can be recycled, if necessary. The bottom product mainly consists of the intermediate fluorides (and unreacted 1,1,1,3,3-pentahalopropane) and the extractant, and these components can be separated each other by a general separation process such as distillation. After the extractant was separated from the bottom product, the remainder containing the intermediate fluorides and unreacted 1,1,1,3,3-pentahalopropane as the main component can be recycled to the fluorination reactor since such remainder can be used as a starting material. On the other hand, the separated extractant can be recycled for the extraction separation step.

In case where 1,1,1,3,3-pentachloropropane is used as the extractant, the fraction including substantially no 1,1,1,3,3-pentafluoropropane (the bottom product) which is obtained through the distillation separation step can be recycled to the reactor as it is. It is because 1,1,1,3,3-pentachloropropane as the extractant can be used as the stating material for the fluorination reaction. Alternatively, the fraction including substantially no 1,1,1,3,3-pentafluoropropane can be returned to the reactor in part, and the remainder can be recycled for the extraction separation step.

Hereinafter, one embodiment of the present invention will be described with referring to the drawing.

As shown in FIG. 1, HF and 1,1,1,3,3-pentahalopropane (in this embodiment, R-240fa described above is used as 1,1,1,3,3-pentahalopropane) are supplied to a reactor 10 through pipes 1 and 2 respectively, wherein antimony pentahalide is situated in the reactor 10 in advance. A temperature inside the reactor is set at no larger than 50° C., e.g. 0 to 30° C. HF and R-240fa are supplied in a liquid state, but the present invention is not limited to this. A reaction temperature is controlled to be no larger than 50° C., e.g. 0 to 30° C. by setting the temperature inside the reactor at an certain degree described above, and fluorination reaction is proceeded at such reaction temperature while HCl produced through the fluorination reaction is taken out the reactor in a gas state. The fluorination reaction is sufficiently proceeded to obtain a reaction solution (or a reaction mixture in a liquid state) 3.

Then, the reaction solution 3 is transferred via a pipe 11 to an extractor 20 where the reaction solution 3 is contacted and mixed with an extractant to form an HF phase 21 and an extractant phase 22 which are immiscible with each other. A solvent ratio S/F (weight basis) is, for example, 0.5 to 2. An extraction temperature is set, for example, at −30 to 30° C. At this stage, the most of unreacted HF and substantially the whole of antimony pentahalide ($SbCl_xF_y$) are distributed into the HF phase 21, and the most of fluorinated products including R-245fa and unreacted R-240fa is distributed into the extractant phase 22. Thereafter, the HF phase 21 is recycled to the reactor 10 through a pipe 23, and the extractant phase 22 is transferred to the first distillation column 30 through a pipe 24. It is noted that the HF phase 21 and the extractant phase 22 are shown as the upper and lower phases respectively in FIG. 1, but these phases may be inverted depending on the kind of the extractant to be used.

In the first distillation column 30, at first, the minimum azeotrope consisting of R-245fa and HF is distilled out from the top of the first column through a pipe 32 by azeotropic distillation and recycled to the reactor 10. In such distillation separation, a distillation temperature is, for example, set at 13 to 50° C. (at a pressure of 0.1 to 0.5 MPa (abs.)), and in this case a molar ratio of R-245fa to HF is in 1:2 to 1:1. The aimed product R-245fa including substantially no HF is subsequently distilled from the top and is taken out through a pipe 31. The pipes 31 and 32 are shown as discrete ones, but they may be formed into a single pipe. The remainder in the form of a bottom product which is resulted from removal of HF and R-245fa by the distillation is transferred to the second distillation column 40 through a pipe 33. The bottom product mainly contains the extractant and the intermediate fluorides of R-244 and R-243.

In the second distillation column 40, the intermediate fluorides are distilled from the top of the second column and recycled to the reactor 10 through a pipe 41. On the other hand, a bottom product of the remainder after the distillation, which consists mainly of the extractant, is transferred through pipes 42 and 11 for recycling to the extraction separation step.

In other embodiment, when the extractant is 1,1,1,3,3-pentachloropropane in especial, the bottom product of the second distillation column 40 is not only recycled through the pipe 11 for the extraction separation step but also recycled to the reactor 10 through a pipe 50 in parts. In further embodiment, the second distillation column 40 may be omitted, and the bottom product of the first distillation column 30 can be recycled in whole through a pipe 51, a part of the pipe 42 and the pipe 50 to the reactor 10, or the bottom product taken through the pipe 51 is returned to the reactor in part while the remainder is recycled through the pipe 11 for the extraction separation step.

Although the present invention has been explained as above with reference to some embodiments, the present invention is not limited to such embodiments and can be modified in various ways within a scope of the invention.

Industrial Applicability

According to the present invention, there can be provided a new and economical process for producing 1,1,1,3,3-pentafluoropropane (R-245fa) which process includes a reaction step for fluorinating 1,1,1,3,3-pentahalopropane with HF in the presence of antimony pentahalide as catalyst, wherein corrosion of a reactor for the reaction is effectively alleviated and R-245fa is obtained with a high selectivity.

EXAMPLES

Example 1

Into an autoclave having a size of 100 ml, 10 g (0.056 mole) of antimony pentafluoride and 50 g (2.5 mole) of HF were introduced. While keeping a temperature inside the autoclave (reactor) at about 0° C. in order to hold a reaction temperature at that temperature and keeping a pressure at about 0.5 MPa, 80 g (0.37 mole) of 1,1,1,3,3-pentachloropropane which belongs to 1,1,1,3,3-pentahalopropane was supplied into the reactor over one hour, so that fluorination reaction was conducted in a liquid phase. Though not only the liquid phase but also a gas phase existed in the autoclave, the amounts of the raw materials (i.e. 1,1,1,3,3-pentahalopropane and HF), fluorinated products and the antimony pentahalide catalyst contained in the gas phase are negligible compared to those in the liquid phase. Therefore, it can be considered that substantially whole of the raw materials and the fluorinated products and antimony pentahalide were contained in the liquid phase, and the liquid phase corresponded to a reaction system. (Such consideration is similarly applicable to following examples.) When 1,1,1,3,3-pentachloropropane was assumed to be fluorinated and changed to R-245fa in whole, an amount of unreacted HF remaining after the reaction could be calculated as 13 g (0.65 mole) in theory by considering consumption through the fluorination reaction. However, more amount of HF than thus calculated value is supposed to exist indeed, since the fluorination of 1,1,1,3,3-pentachloropropane would not be proceeded completely. Thus, it was confirmed that the amount of HF was maintained at an amount not less than ten times by mole as large as that of antimony pentafluoride as the catalyst in this case until the end point of the reaction. After maintaining such temperature and pressure during two hours from the beginning of the introduction of 1,1,1,3,3-pentachloropropane while discharging HCl which was emitted into the gas phase through the reaction, 50 ml of perfluoro-2-methylpentane was further introduced into the reactor as an extractant (or an extracting solvent). Then, a reaction solution was withdrawn together with the extractant from the reactor through an insert tube into a sealed tube made of fluororesin. Thereafter, the mixed solution was located at a temperature of about 0° C. in the sealed tube to form an HF phase (11 g) and an extractant phase (130 g) which were immiscible with and separated from each other, so that the extractant phase enriched with R-245fa was obtained.

The conditions of the reaction and the extraction of this example are listed below:

| | |
|---|---|
| Reaction Temperature | about 0° C. |
| Reaction Pressure | about 0.5 MPa (abs.) |
| HF/SbF$_5$ (the initial point) | about 45 (molar basis) |
| HF/SbF$_5$ (the end point) | 11 or more (molar basis) |
| HF/1,1,1,3,3-pentachloropropane (the initial point) | about 6.8 (molar basis) |
| Extractant | perfluoro-2-methylpentane |
| Extraction Temperature | about 0° C. |
| Solvent Ratio S/F | about 1.5 (weight basis) |

In order to measure the concentration of HF in thus resulted extractant phase, HF contained in the extractant phase was withdrawn into water. The HF content in the water phase was quantitated with an analysis by means of an ion chromatography, and the fluorinated products contained in the remaining extractant phase was quantitated with an analysis by means of a gas chromatography. According to the results, HF and the organic compounds contained in the extractant phase were as follows:

| | |
|---|---|
| HF | 1.5 g (0.075 mole) |
| R-245fa | 45.2 g (0.33 mole) |
| R-244fa | 0.86 g (0.005 mole) |
| R-243fa | 0.55 g (0.003 mole) |

According to the results listed above, it was demonstrated that R-245fa could be produced with a high selectivity in spite of low reaction temperature (which was 0° C. in this example) by maintaining the molar amount of HF at no less than 5 times, and preferably no less than 10 times as large as that of antimony pentahalide.

Example 2

A mixture having a composition ratio similar to that of the extractant phase obtained in Example 1 and consisting of compounds listed below was prepared:

| | |
|---|---|
| HF | 15 g (0.75 mole) |
| R-245fa | 452 g (3.3 mole) |
| R-244fa | 8.6 g (0.05 mole) |
| R-243fa | 5.5 g (0.03 mole) |

The mixture was subjected to a rectification process in batch mode by means of an Oldershaw distillation apparatus made of SUS (stainless steel specified by JIS (Japanese Industrial Standard)) and having thirty stages. At first, 120 g of an azeotrope of R-245fa and HF was distilled out from the top of the apparatus to remove most of HF. Then, 280 g of R-245fa including substantially no HF (of which HF content is not greater than 0.1% by weight) was obtained from the top likewise.

The conditions of the distillation of this example are listed below:

| | |
|---|---|
| Distillation Temperature | about 13° C. |
| Distillation Pressure | about 0.1 MPa (abs.) |
| Composition of Azeotrope | R-245 about 1 mole |
| | HF about 1.8 mole |

Therefore, it was demonstrated that R-245fa including substantially no HF could be readily obtained through the distillation process by removing HF in the form of the azeotrope of HF and R-245fa from the extractant phase which was obtained similarly to the procedure of Example 1.

Example 3

An extractant phase enriched with R-245fa was obtained similarly to the procedure of Example 1 except that the temperature inside the reactor (i.e. the reaction temperature) was changed from 0° C. to 10° C., and the reaction solution was cooled to 0° C. after fluorination reaction and before withdrawing the reaction solution from the reactor.

The conditions of the reaction and the extraction of this example are listed below:

| | |
|---|---|
| Reaction Temperature | about 10° C. |
| Reaction Pressure | about 0.6 MPa (abs.) |
| HF/SbF$_5$ (the initial point) | about 45 (molar basis) |
| HF/SbF$_5$ (the end point) | 11 or more (molar basis) |
| HF/1,1,1,3,3-pentachloropropane (the initial point) | about 6.8 (molar basis) |
| Extractant | perfluoro-2-methylpentane |
| Extraction Temperature | about 0° C. |
| Solvent Ratio S/F | about 1.5 (weight basis) |

The extractant phase obtained as above was subjected to a quantitative analysis as described in Example 1. According to the results, HF and the organic compounds contained in the extractant phase were as follows:

| | |
|---|---|
| HF | 1.5 g (0.075 mole) |
| R-245fa | 46.2 g (0.34 mole) |
| R-244fa | 0.03 g (0.2 milli-mole) |
| R-243fa | 0.04 g (0.2 milli-mole) |

According to the results listed above, it was demonstrated that R-245fa could be produced with a higher selectivity in case of the reaction temperature of 10° C. than that in Example 1 by maintaining the molar amount of HF at no less than 5 times, and preferably no less than 10 times as large as that of antimony pentahalide.

Additionally, the extractant phase obtained through this example was subjected to a distillation with a similar operation as described in Example 2. It was also possible in this example to obtain R-245fa including substantially no HF (of which HF content is not greater than 0.1% by weight).

Example 4

An extractant phase enriched with R-245fa was obtained similarly to the procedure of Example 1 except that the extractant was changed from perfluoro-2-methylpentane to 1,1,1,3,3-pentachloropropane.

The conditions of the reaction and the extraction of this example are listed below:

| | |
|---|---|
| Reaction Temperature | about 0° C. |
| Reaction Pressure | about 0.5 MPa (abs.) |
| HF/SbF$_5$ (the initial point) | about 45 (molar basis) |
| HF/SbF$_5$ (the end point) | 11 or more (molar basis) |
| HF/1,1,1,3,3-pentachloropropane (the initial point) | about 6.8 (molar basis) |
| Extractant | 1,1,1,3,3-pentachloropropane |
| Extraction Temperature | about 0° C. |
| Solvent Ratio S/F | about 1.7 (weight basis) |

The extractant phase obtained as above was subjected to a quantitative analysis as described in Example 1. According to the results, HF and the organic compounds contained in the extractant phase were as follows:

| | |
|---|---|
| HF | 2.2 g (0.11 mole) |
| R-245fa | 38.3 g (0.29 mole) |
| R-244fa | 0.96 g (0.006 mole) |
| R-243fa | 0.65 g (0.004 mole) |

According to the results listed above, it was demonstrated that R-245fa could be extracted even when 1,1,1,3,3-pentachloropropane is used as the extractant which is also used as the starting material, and that R-245fa could be produced with a high selectivity.

Additionally, the extractant phase obtained through this example was subjected to a distillation with a similar operation as described in Example 2. It was also possible in this example to obtain R-245fa including substantially no HF (of which HF content is not greater than 0.1% by weight).

Example 5

An extractant phase enriched with R-245fa was obtained similarly to the procedure of Example 1 except that the extractant was changed from perfluoro-2-methylpentane to perfluorohexane.

The conditions of the reaction and the extraction of this example are listed below:

| | |
|---|---|
| Reaction Temperature | about 0° C. |
| Reaction Pressure | about 0.5 MPa (abs.) |
| HF/SbF$_5$ (the initial point) | about 45 (molar basis) |
| HF/SbF$_5$ (the end point) | 11 or more (molar basis) |
| HF/1,1,1,3,3-pentachloropropane (the initial point) | about 6.8 (molar basis) |
| Extractant | perfluorohexane |
| Extraction Temperature | about 0° C. |
| Solvent Ratio S/F | about 1.5 (weight basis) |

The extractant phase obtained as above was subjected to a quantitative analysis as described in Example 1. According to the results, HF and the organic compounds contained in the extractant phase were as follows:

| | |
|---|---|
| HF | 3.1 g (0.155 mole) |
| R-245fa | 36.2 g (0.27 mole) |
| R-244fa | 0.96 g (0.006 mole) |
| R-243fa | 0.66 g (0.004 mole) |

According to the results listed above, it was demonstrated that R-245fa could be extracted even when perfluorohexane is used as the extractant and that R-245fa could be produced with a high selectivity.

Additionally, the extractant phase obtained through this example was subjected to a distillation with a similar operation as described in Example 2. It was also possible in this example to obtain R-245fa including substantially no HF (of which HF content is not greater than 0.1% by weight).

Example 6

An extractant phase enriched with R-245fa was obtained similarly to the procedure of Example 1 except that the temperature inside the reactor was changed from 0° C. to 30° C., the extractant was changed from perfluoro-2-methylpentane to perfluorotributylamine, and the reaction solution was cooled to 0° C. after fluorination reaction and before withdrawing the reaction solution from the reactor.

The conditions of the reaction and the extraction of this example are listed below:

| | |
|---|---|
| Reaction Temperature | about 30° C. |
| Reaction Pressure | about 0.5 MPa (abs.) |
| HF/SbF$_5$ (the initial point) | about 45 (molar basis) |
| HF/SbF$_5$ (the end point) | 11 or more (molar basis) |
| HF/1,1,1,3,3-pentachloropropane (the initial point) | about 6.8 (molar basis) |
| Extractant | perfluorotributylamine |
| Extraction Temperature | about 0° C. |
| Solvent Ratio S/F | about 1.5 (weight basis) |

The extractant phase obtained as above was subjected to a quantitative analysis as described in Example 1. According to the results, HF and the organic compounds contained in the extractant phase were as follows:

| | |
|---|---|
| HF | 3.6 g (0.18 mole) |
| R-245fa | 28.8 g (0.21 mole) |
| R-244fa | 0.01 g (0.006 mole) |
| R-243fa | 0.02 g (0.004 mole) |

According to the results listed above, it was demonstrated that R-245fa could also be extracted and produced with a high selectivity in this Example.

Additionally, the extractant phase obtained through this example was subjected to a distillation with a similar operation as described in Example 2. It was also possible in this example to obtain R-245fa including substantially no HF (of which HF content is not greater than 0.1% by weight).

Example 7

Into an autoclave having a size of 100 ml, 11.8 g (0.056 mole) of antimony dichlorotrifluoride (SbCl$_2$F$_3$) and 52 g (2.6 mole) of HF were introduced. While keeping a temperature inside the autoclave (reactor) at about 0° C. in order to hold a reaction temperature at that temperature and keeping a pressure at about 0.5 MPa, 80 g (0.37 mole) of 1,1,1,3,3-pentachloropropane which belongs to 1,1,1,3,3-pentahalopropane was supplied into the reactor over one hour, so that fluorination reaction was conducted in a liquid phase. When 1,1,1,3,3-pentachloropropane was assumed to be fluorinated and changed to R-245fa in whole, an amount of unreacted HF remaining after the reaction could be calculated as about 13 g (0.65 mole) in theory by considering consumption through the fluorination reaction (which comprises not only the fluorination reaction of 1,1,1,3,3-pentachloropropane but also a fluorination reaction of SbCl$_2$F$_3$ as the catalyst in this example). However, more amount of HF than thus calculated value is supposed to exist indeed, since the fluorination of 1,1,1,3,3-pentachloropropane would not be proceeded completely. Thus, it was confirmed that the amount of HF was maintained at an amount not less than ten times by mole as large as that of antimony dichlorotrifluoride as the catalyst in this case until the end point of the reaction. After maintaining that temperature and pressure during two hours from the beginning of the introduction of 1,1,1,3,3-pentachloropropane while discharging HCl which was emitted into the gas phase through the reaction, 50 ml of perfluoro-2-methylpentane was further introduced into the reactor as an extractant (or an extracting solvent). Then, a reaction solution was withdrawn together with the extractant from the reactor through an insert tube into a sealed tube made of fluororesin. Thereafter, the mixed solution was located at a temperature of about 0° C. in the sealed tube to form an HF phase (11 g) and an extractant phase (130 g) which were immiscible with and separated from each other, so that the extractant phase enriched with R-245fa was obtained.

The conditions of the reaction and the extraction of this example are listed below:

| | |
|---|---|
| Reaction Temperature | about 0° C. |
| Reaction Pressure | about 0.5 MPa (abs.) |
| HF/SbCl$_2$F$_3$ (the initial point) | about 45 (molar basis) |
| HF/SbF$_5$ (the end point) | 11 or more (molar basis) |
| HF/1,1,1,3,3-pentachloropropane (the initial point) | about 6.8 (molar basis) |
| Extractant | perfluoro-2-methylpentane |
| Extraction Temperature | about 0° C. |
| Solvent Ratio S/F | about 1.5 (weight basis) |

In order to measure the concentration of HF in thus resulted extractant phase, HF contained in the extractant phase was withdrawn into water. The HF content in the water phase was quantitated with an analysis by means of an ion chromatography, and the fluorinated products contained in the remaining extractant phase was quantitated with an analysis by means of a gas chromatography. According to the results, HF and the organic compounds contained in the extractant phase were as follows:

| | |
|---|---|
| HF | 1.5 g (0.075 mole) |
| R-245fa | 44.9 g (0.33 mole) |
| R-244fa | 0.98 g (0.007 mole) |
| R-243fa | 0.58 g (0.003 mole) |

According to the results listed above, it was demonstrated that R-245fa could be produced with a high selectivity in spite of low reaction temperature (which was 0° C. in this example) by maintaining the molar amount of HF at no less than 5 times, and preferably no less than 10 times as large as that of antimony pentahalide.

(Corrosion Test)

In order to exhibit that corrosion of the reactor can be effectively reduced by the present invention, corrosion tests were conducted under a condition corresponding to that of the reaction solution. Test pieces made of a material for the reactor (10 mm×20 mm×1 mm) were immersed in a solution of 1% by mole of SbF$_5$/HF in a pressurized vessel lined with fluororesin for ten days. Corrosion Rates were estimated based on change in weight of the test pieces between before and after the immersion while changing materials of the test pieces and temperature of the solution. It is noted that the corrosion rates (mm/year) were calculated according to the equation as follow:

$$\text{(Corrosion Rate)} = \frac{((\text{Weight before Immersion}) - (\text{Weight after Immersion})) \times 365}{(\text{Specific Gravity}) \times (\text{Surface Area}) \times 10}$$

The results are shown in Tables 1 and 2. In these Tables, results conditioned with a with a temperature without a scope of the present invention are also shown as comparative examples.

TABLE 1

Effect of Temperature to Corrosion Rate

| Material | Temperature (° C.) | Corrosion Rate (mm/year) |
|---|---|---|
| Hastelloy C-22 | 0 | 0.01 |
| | 10 | 0.02 |
| | 30 | 0.08 |
| | 80 (Comparative Example) | 0.36 |
| | 100 (Comparative Example) | 0.55 |

TABLE 2

Effect of Temperature to Corrosion Rate

| | Corrosion Rate (mm/year) | |
|---|---|---|
| Material | 10° C. | 100° C. (Comparative Example) |
| Hastelloy C-22 | 0.02 | 0.55 |
| Monel 400 | 0.56 | 8.72 |
| Inconel 600 | 0.39 | 5.36 |
| SUS 316 | 1.96 | unmeasurable (disappeared) |

Referring Tables 1 and 2, it can be understood that the corrosion rates are very low at a low temperature less 5 than 50° C. Therefore, it is apparent that the corrosion of the reactor may be retarded by conducting the fluorination reaction in the presence of antimony pentahalide at a temperature less than 50° C.

What is claimed is:

1. A process for depressing corrosion of a metal material of a reactor while producing 1,1,1,3,3-pentafluoropropane, wherein said process comprises:

a liquid-phase reaction step for fluorination of 1,1,1,3,3-pentahalopropane with HF, wherein at least one of the halogen atoms in said 1,1,1,3,3-pentahalopropane is not F, wherein said 1,1,1,3,3-pentahalopropane is fluorinated in the presence of antimony pentahalide as a catalyst in said reactor to obtain a reaction mixture comprising at least 1,1,1,3,3-pentafluoropropane and antimony pentahalide as the catalyst, wherein the fluorination is conducted at a reaction temperature at less than 50° C. while HF exists in a reaction system in an amount of at least 5 times by mole as large as an amount of said antimony pentahalide; and depressing corrosion of the metal material of said reactor.

2. The process for depressing corrosion of a metal material of a reactor of claim 1, wherein said metal material comprises a nickel-chromium-molybdenum-tungsten alloy.

3. The process for depressing corrosion of a metal material of a reactor of claim 1, wherein said metal material is a Ni-based material which has corrosion resistance.

4. The process for depressing corrosion of a metal material of a reactor of claim 1, wherein said metal material comprises 20.0–22.5 of Cr, 12.5–14.5 of Mo, 2.5–3.5 of W, 2.0–6.0 of Fe, $\leq 0.010$ of C, $\leq 0.50$ of Mn, $\leq 0.08$ of Si, $\leq 0.35$ of V, $\leq 0.02$ of P, $\leq 0.02$ of S, and the balance being Ni.

* * * * *